(12) United States Patent
Kadowaki et al.

(10) Patent No.: US 10,557,848 B2
(45) Date of Patent: Feb. 11, 2020

(54) POLYMER MICROPARTICLE FOR CARRYING PHYSIOLOGICALLY ACTIVE SUBSTANCE AND METHOD FOR PREPARING SAME

(71) Applicants: LSI Medience Corporation, Tokyo (JP); National University Corporation Chiba University, Chiba (JP)

(72) Inventors: Atsushi Kadowaki, Tokyo (JP); Tatsuo Taniguchi, Chiba (JP); Yusuke Sasaki, Chiba (JP); Naho Konishi, Chiba (JP)

(73) Assignees: LSI MEDIENCE CORPORATION, Tokyo (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 74 days.

(21) Appl. No.: 15/507,858

(22) PCT Filed: Sep. 2, 2015

(86) PCT No.: PCT/JP2015/074913
§ 371 (c)(1),
(2) Date: Mar. 1, 2017

(87) PCT Pub. No.: WO2016/035806
PCT Pub. Date: Mar. 10, 2016

(65) Prior Publication Data
US 2017/0299580 A1    Oct. 19, 2017

(30) Foreign Application Priority Data
Sep. 2, 2014   (JP) ................................ 2014-178458

(51) Int. Cl.
| C08F 2/24 | (2006.01) |
| C08F 2/38 | (2006.01) |
| C08F 293/00 | (2006.01) |
| C08F 297/00 | (2006.01) |
| G01N 33/545 | (2006.01) |

(52) U.S. Cl.
CPC ....... G01N 33/545 (2013.01); C08F 293/005 (2013.01)

(58) Field of Classification Search
CPC .......... C08F 2/24; C08F 2/38; C08F 293/005; C08F 297/00; G01N 33/545
See application file for complete search history.

(56) References Cited

U.S. PATENT DOCUMENTS

| 5,543,158 A | 8/1996 | Gref et al. |
| 5,565,215 A | 10/1996 | Gref et al. |
| 5,578,325 A | 11/1996 | Domb et al. |
| 6,007,845 A | 12/1999 | Domb et al. |
| 2004/0018564 A1 | 1/2004 | Kyoshi et al. |
| 2009/0014682 A1 | 1/2009 | Takahashi et al. |
| 2010/0197042 A1 | 8/2010 | Sawai et al. |
| 2010/0304503 A1 | 12/2010 | Taniguchi et al. |
| 2011/0184155 A1 | 7/2011 | Takahashi et al. |
| 2013/0149538 A1 | 6/2013 | Takahashi et al. |
| 2013/0164761 A1 | 6/2013 | Takahashi et al. |

FOREIGN PATENT DOCUMENTS

| CN | 101542286 A | 9/2009 |
| EP | 2088428 A1 | 8/2009 |
| JP | S64-54003 A | 3/1989 |
| JP | S64-065102 A | 3/1989 |
| JP | H09-504308 A | 4/1997 |
| JP | 2003231648 A | 8/2003 |
| JP | 2004059696 A | 2/2004 |
| JP | 2004061301 A | 2/2004 |
| JP | 2007-100035 A | 4/2007 |
| JP | 2007145985 A | 6/2007 |
| WO | 9200283 A2 | 1/1992 |
| WO | 2008047799 A1 | 4/2008 |

OTHER PUBLICATIONS

Muñoz-Bonilla, A. et al. Macromolecules vol. 44 pp. 4282-4290 (May 2011).*
Palusiak, M. et al. Journal of Molecular Structure vol. 642 pp. 97-104 (Dec. 2002).*
Sasaki, Y. et al. Colloids and Surfaces A: Physicochemical and Engineering Aspects vol. 482 pp. 68-78 (Apr. 2015).*

(Continued)

*Primary Examiner* — Irina S Zemel
*Assistant Examiner* — Jeffrey S Lenihan
(74) *Attorney, Agent, or Firm* — Heslin Rothenberg Farley & Mesiti P.C.

(57) ABSTRACT

Provided are novel polymer particles for carrying a physiologically active substance and a method of preparing the same. The polymer particles for carrying a physiologically active substance can provide an analytical reagent, which has high analytical precision and sensitivity and can be stably prepared; can easily and precisely control the amount of functional groups carrying the physiologically active substance; can introduce, onto the surface of latex particles, a hydrophilic compound for inhibiting a nonspecific reaction; and can be prepared to have a narrow and uniform particle size distribution. The polymer particles for carrying a physiologically active substance are obtained by polymerizing a monomer, a radical polymerization initiator, and an emulsifier, and the emulsifier is an amphiphilic block polymer of the general formula (1):

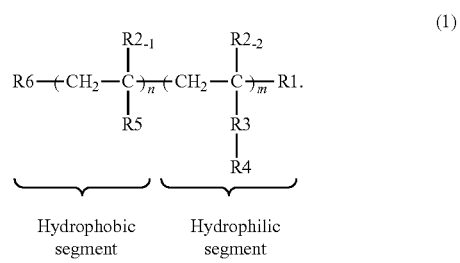

9 Claims, 1 Drawing Sheet

(56) References Cited

OTHER PUBLICATIONS

Patent Cooperation Treaty, International Search Report for PCT/JP2015/074913 dated Nov. 24, 2015, 2 pages.
Patent Cooperation Treaty, Written Opinion of the International Searching Authority for PCT/JP2015/074913 dated Nov. 24, 2015, 5 pages.
Sasaki et al., "Preparation of Polymer Particles from Nanocmulsions Obtained by Phase Inversion Temperature Method," May 2014, 4 pages, Polymer Preprints, Japan, vol. 63, No. 1 (1Pa039).
Sasaki et al., "Preparation of O/W emulsions via phase inversion emulsification using amphiphilic block polymers synthesized by atom transfer radical polymerization," Aug. 2013, 3 pages, Polymer Preprints Japan, vol. 62, No. 2 (2Pb056).
Supplemental European Search Report for European Patent Application No. 15837788.7, Regional Stage entry of PCT/JP2015/074913, dated Mar. 19, 2018.
Markus Antonietti,Katharina Landfester, Polyreactions in miniemulsions, Prog. Polym. Sci., 2002, vol. 27,No. 4, p. 689-757, https://doi.org/10.1016/S0079-6700(01)00051-X.
Liat Spernath, Shlomo Magdassi. A new method for preparation of poly-lauryl acrylate nanoparticles from nanoemulsions obtained by the phase inversion temperature process. Polym. Adv. Technol., 2007, vol. 18, p. 705-711, https://doi.org/10.1002/pat. 947.
Translation of Japanese Office Action dated May 16, 2019.

\* cited by examiner

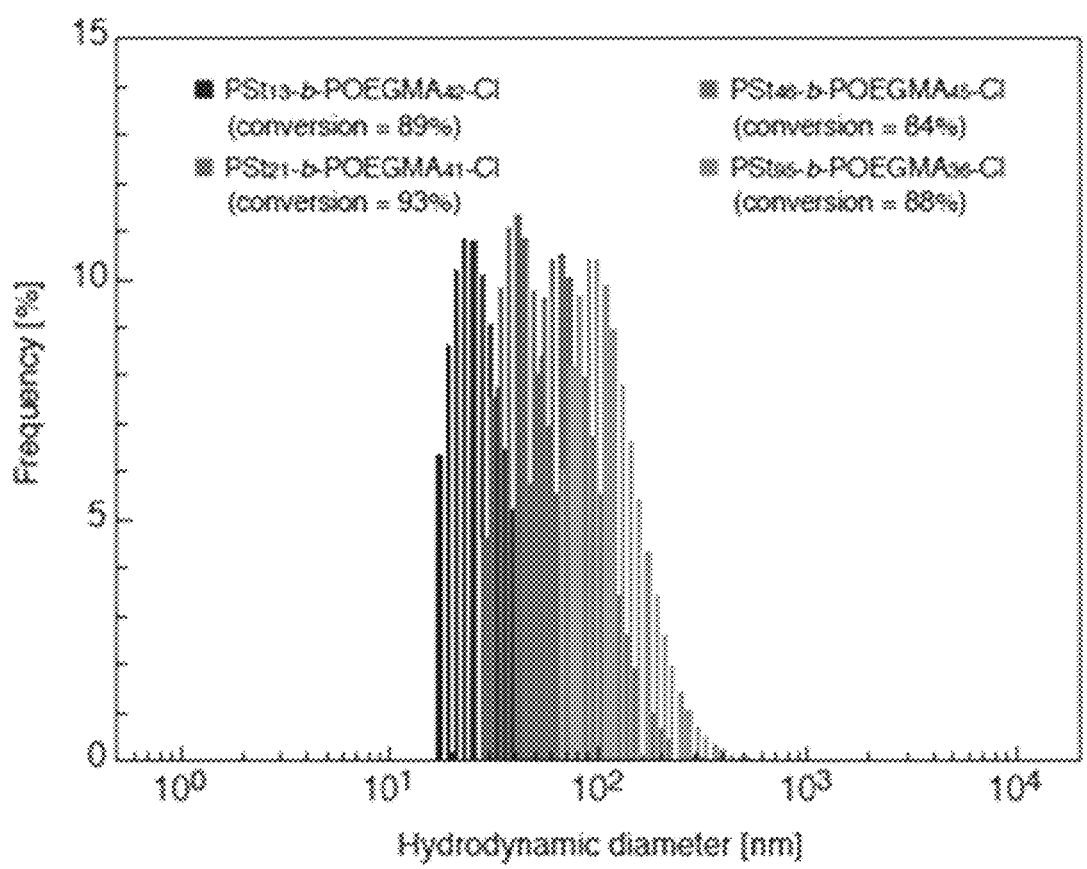

POLYMER MICROPARTICLE FOR CARRYING PHYSIOLOGICALLY ACTIVE SUBSTANCE AND METHOD FOR PREPARING SAME

CROSS REFERENCE TO RELATED APPLICATIONS

This application is a national stage filing under section 371 of International Application No. PCT/JP2015/074913, filed Sep. 2, 2015, and published in Japanese on Mar. 10, 2016, as WO 2016/035806 A1, and claims priority of Japanese Patent Application No. 2014-178458, filed on Sep. 2, 2014, the entire disclosure of these applications being hereby incorporated herein by reference.

TECHNICAL FIELD

The present invention relates to polymer particles for carrying a physiologically active substance, and a method of preparing the same.

The term "analysis" as used herein includes "measurement" to quantitatively or semi-quantitatively determine the amount of a substance to be analyzed, and "detection" to judge the presence or absence of the substance to be analyzed.

BACKGROUND ART

Currently, in the field of clinical diagnostic testing, it is required to measure a wide variety of substances that serve as indicators of disease diagnosis for a large number of specimens in a short time and with high accuracy, and to feed back the results quickly and accurately to the treatment site. For example, accurate quantification of a trace amount of an analyte has been carried out many times by an analytical system in which physiologically active substances (proteins such as antibodies, enzymes, receptors, or the like; antigens; nucleic acids such as DNA, RNA, or the like; sugar chains; or the like) are bound to the particle surfaces, such as an immunological measurement utilizing an antigen-antibody reaction. In particular, as a method for improving the detection sensitivity and accuracy, a latex agglutination method utilizing particles in which an antigen or antibody against a substance to be analyzed is carried on the surface of synthetic polymer (so-called latex) particles, such as polystyrene, is known. The latex agglutination method is a method in which a substance to be analyzed is measured in a short time by visually or optically detecting the degree of agglutination of latex particles caused by a reaction of the substance to be analyzed with an antigen or antibody bound to latex particles.

A sandwich method, in which the latex particles are made of magnetic particles, and a substance to be analyzed is trapped with the first antibody bound to the magnetic particles, and an unreacted substance and the like is washed while being accumulated using a magnet (so-called B/F separation), and analysis is carried out by adding the second antibody labelled with a substance capable of generating a signal, such as an enzyme, a fluorescent agent, or the like, is also frequently used.

Many substances to be analyzed, which are quantified by an antigen-antibody reaction, are generally trace components contained in a biological sample, and it emphasizes the quantitative performance in the low-concentration region. However, since the concentration of the substance to be measured sometimes shows a high value abnormally, depending on the degree of disease progression, there is a demand for a reagent capable of accurately measuring from a low value to a high value.

When latex particles are used in the latex agglutination method or the sandwich method, it is necessary to immobilize an antigen or antibody on the surface of the latex particles. As the immobilizing method, a method in which the latex particles are physically or chemically carried is used. For example, a method in which an antigen or antibody is directly immobilized on the latex particles by physical adsorption, or a method in which an antigen or antibody is bonded to the surface of the latex particles, by a covalent bond via a functional group, such as a carboxyl group, a maleimide group, an amino group, a mercapto group, a hydroxyl group, an aldehyde group, an epoxy group, or the like, is used.

In comparison with the physically binding method, the chemically binding method is superior, because the antibody is bonded on the surface of the latex particles via a covalent bond, and can be stably carried on the surface. Various methods of bonding a functional group to the surface of latex particles have been reported, but there is a problem that the control of a variation in production lot and the amount of the bonded functional group are difficult, and particles that stably and accurately carry a physiologically active substance cannot be prepared (Patent literatures 1 and 2).

Further, various methods for quantifying the amount of functional groups on the surface of latex particles have been reported, and, for example, in a method wherein acid-base titration, which is used for the quantification of a carboxyl group, is performed, and quantification is carried out from a change in electrical conductivity, when the amount of the functional group is extremely small, accurate quantification is difficult. Since the latex particles used in clinical diagnosis are small, and the amount of the functional group becomes small, and thus, accurate quantification becomes difficult, and it is a problem that stable supply to produce clinical diagnostic reagents cannot be done.

Further, it is important for an application to biomaterials, such as clinical diagnostic agents or the like, to control the distance between the latex particle surface and the functional group for carrying a physiologically active substance, for binding a biological sample. Conventionally, there is a technique wherein a compound having double bonds, and further having functional groups via a hydrophilic polymer such as polyethylene glycol, as a macromonomer, is copolymerized with a monomer such as styrene, to bond on the latex surface. However, there is a problem that it is difficult to control the amount of the bound functional group, and to obtain latex particles having small production lot to lot difference.

Further, as a problem of the latex agglutination method, there may be mentioned a non-specific reaction, in which non-specific agglutination occurs by adsorbing contaminants other than the substance to be measured on the surface of the latex particles (non-specific adsorption), and as a result, this non-specific agglutination is quantified as the substance to be measured.

As a general method of inhibiting a non-specific reaction, there may be mentioned a method in which bovine serum albumin (BSA) or sugar is previously adsorbed to latex particles. However, it is difficult to uniform the adsorbed amount of BSA or sugar, or lot to lot difference of BSA, which is a protein derived from an organism, and it is difficult to stably supply an analytical reagent by a latex agglutination method (Patent literature 3).

Further, a method in which an antigen or antibody against the substance to be analyzed is present at the time of synthesis of polymer particles, and the polymer particles are modified with the antigen or antibody, to inhibit the non-specific adsorption, which previously occurred, has been reported, but it is not sufficient (Patent literature 4).

As a method of inhibiting non-specific adsorption, a method in which a compound having a polymerizable double bond at the end of polyethylene glycol, which is known to be effective for inhibition of a non-specific reaction, is used as a monomer, to synthesize polymer particles, is known, but it is not sufficient (Patent literature 5).

A technique of inhibiting non-specific adsorption wherein a monomer effective for inhibition of non-specific adsorption is allowed to be present during polymerization, but it is not sufficient (Patent literature 6).

Recently, a method of inhibiting a non-specific reaction by adsorbing a block master (JSR Corporation), in which a hydrophobic unit is incorporated into polyethylene glycol, to the surface of latex particles is developed. However, there are problems that lot difference increases due to the complication of a preparation step of an immunological analytic reagent, and that it is difficult to quantify the modified amount of the block master.

Therefore, latex particles used in clinical diagnostic reagents are required to improve the stability of the manufacture of clinical diagnostic reagents and the accuracy of clinical diagnostic reagents, but it has not been achieved yet.

CITATION LIST

Patent Literature

[Patent literature 1] Japanese Unexamined Patent Publication (Kokai) No. 2004-59696
[Patent literature 2] Japanese Unexamined Patent Publication (Kokai) No. 2004-61301
[Patent literature 3] Japanese Unexamined Patent Publication (Kokai) No. 2007-145985
[Patent literature 4] WO2008/047799
[Patent literature 5] Japanese Unexamined Patent Publication (Kokai) No. 2003-231648
[Patent literature 6] Japanese Unexamined Patent Publication (Kokai) No. 2007-100035

SUMMARY OF INVENTION

Technical Problem

The inventors conducted intensive studies to overcome the problems of synthesis of latex particles, and found novel polymer particles for carrying a physiologically active substance, capable of simply and accurately controlling the amount of a functional group for carrying a physiologically active substance, capable of introducing a hydrophilic compound, which inhibits a non-specific reaction, onto the surface of latex particles, and capable of preparing polymer particles having a narrow and uniform particle size distribution; and the method of preparing the same.

The problem of the present invention is to provide novel polymer particles for carrying a physiologically active substance, capable of providing an analytical reagent, which has high analysis accuracy and sensitivity and can be stably prepared, capable of simply and accurately controlling the amount of a functional group for carrying a physiologically active substance, capable of introducing a hydrophilic compound, which inhibits a non-specific reaction, onto the surface of latex particles, and capable of preparing polymer particles having a narrow and uniform particle size distribution; and the method of preparing the same.

Solution to Problem

Conventionally, only methods, in which only one problem could be solved, but it could not be solved significantly, and it was very complicated and difficult, were known. Surprisingly, the problems (in particular, three problems) can be solved simultaneously and more conveniently, by using a polymer emulsifier of the general formula (1), which has a functional group for carrying a physiologically active substance in a molecule, which is an amphiphilic block polymer consisting of a hydrophilic segment and a hydrophobic segment, and of which the hydrophilic segment inhibits a non-specific reaction, when a miniemulsion polymerization is carried out using a monomer, a radical polymerization initiator, and an emulsifier.

The present invention relates to:
[1] polymer particles for carrying a physiologically active substance, said polymer particles being obtained by polymerizing a monomer, a radical polymerization initiator, and an emulsifier, wherein the emulsifier is an amphiphilic block polymer of the general formula (1):

[Chem. 1]

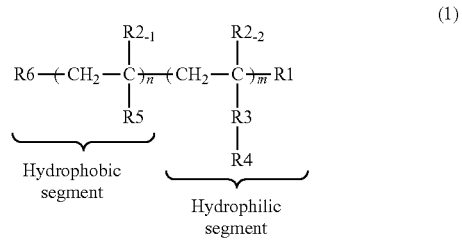

(1)

wherein n is an integer of 5 or more,
m is an integer of 5 or more,
R1 and R4 are independent, and at least one of R1 and R4 is a functional group for carrying a physiologically active substance,
$R2_{-1}$ and $R2_{-2}$ are independently a hydrogen atom, a methyl group, an ethyl group, or a propyl group,
R3 is a functional group derived from a hydrophilic compound,
R5 is a functional group imparting hydrophobicity, and
R6 is a halogen atom, or a functional group derived from the initiator in the synthesis of the emulsifier,
[2] the polymer particles for carrying a physiologically active substance of [1], wherein R1 or R4 is a group selected from the group consisting of a carboxyl group, a maleimide group, an amino group, a mercapto group, a hydroxyl group, an aldehyde group, and an epoxy group,
[3] the polymer particles for carrying a physiologically active substance of [1] or [2], wherein the hydrophilic compound in R3 is a compound selected from the group consisting of oligoethylene glycol, polyethylene glycol, a 2-methacryloyloxyethyl phosphorylcholine polymer, polyvinyl alcohol, polyvinyl pyrrolidone, polyamino acids, polypeptides, monosaccharides, and polysaccharides,
[4] the polymer particles for carrying a physiologically active substance of any one of [1] to [3], wherein R5 is one or more functional groups selected from the group consisting of a hydrogen atom, a halogen atom, a methyl group, an ethyl group, a propyl group, a substituted or unsubstituted aromatic compound group, a carbonyl group, an amide group, an amino group, an aldehyde group, and a keto group, and a functional group derived from each compound of amines, aldehydes, ketones, and ethers,

[5] the polymer particles for carrying a physiologically active substance of any one of [1] to [4], the molecular weight of the emulsifier is 1,000 to 1,000,000,

[6] the polymer particles for carrying a physiologically active substance of any one of [1] to [5], the molecular weight of the hydrophilic segment is 500 to 500,000,

[7] the polymer particles for carrying a physiologically active substance of any one of [1] to [6], the molecular weight of the hydrophobic segment is 500 to 500,000,

[8] a method of preparing polymer particles for carrying a physiologically active substance, characterized in that an emulsifier used in a miniemulsion polymerization using a monomer, a radical polymerization initiator, and the emulsifier is a compound of the general formula (1):

[Chem. 2]

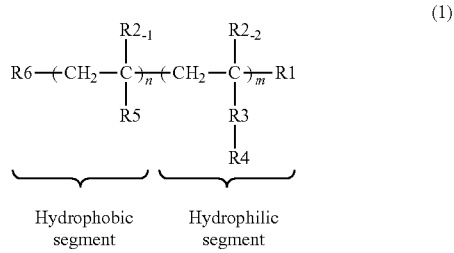

(1)

wherein n is an integer of 5 or more,
m is an integer of 5 or more,
R1 and R4 are independent, and at least one of R1 and R4 is a functional group for carrying a physiologically active substance,
$R2_{-1}$ and $R2_{-2}$ are independently a hydrogen atom, a methyl group, an ethyl group, or a propyl group,
R3 is a functional group derived from a hydrophilic compound,
R5 is a functional group imparting hydrophobicity, and
R6 is a halogen atom, or a functional group derived from the initiator in the synthesis of the emulsifier,

[9] the method of [8], wherein the synthesis of the emulsifier is a control/living radical polymerization or an ionic polymerization, and

[10] the method of [8] or [9], wherein the miniemulsion polymerization is a phase inversion emulsification method.

Advantageous Effects of Invention

According to the present invention, novel polymer particles for carrying a physiologically active substance, capable of simply and accurately controlling the amount of a functional group for carrying a physiologically active substance, capable of introducing a hydrophilic compound, which inhibits a non-specific reaction, onto the surface of latex particles, and capable of preparing polymer particles having a narrow and uniform particle size distribution; and the method of preparing the same

BRIEF DESCRIPTION OF THE DRAWINGS

The FIGURE shows particle size distributions of latex particles. The horizontal axis represents the particle size, and the vertical axis represents the proportion of particles.

DESCRIPTION OF EMBODIMENTS

The polymer particles for carrying a physiologically active substance of the present invention comprises a monomer, a radical polymerization initiator, and an emulsifier, and the emulsifier has the features described below.

The emulsifier, which can be used in the present invention, has at least the following features:
[1] that it is an amphiphilic block polymer consisting of a hydrophilic segment and a hydrophobic segment, and
[2] that it has one or more functional groups for carrying a physiologically active substance at one or more ends of the hydrophilic segment (at one or more of R1 and R4).

The emulsifier and the monomer may be covalently bonded to each other by a miniemulsion polymerization reaction, or may not be covalently bonded. For example, when the emulsifier has one or more polymerizable double bonds within the hydrophobic segment or at the end(s) of the hydrophobic segment, the emulsifier can be covalently bonded to the polymer particles. On the other hand, since the hydrophobic segment of the emulsifier strongly interacts with the polymer particles, the emulsifier added at the time of the polymerization reaction is strongly bonded to the polymer particles, and a stable state can be maintained even without covalent bonding, and therefore, it is preferable because the polymerization reaction is easy.

The emulsifier, which can be used in the present invention, is represented by the following general formula (1):

[Chem. 3]

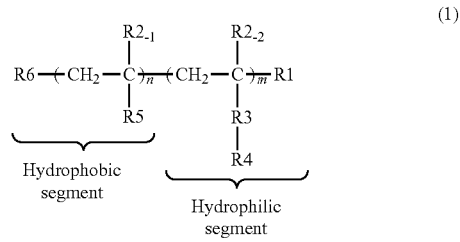

(1)

wherein n is an integer of 5 or more,
m is an integer of 5 or more,
at least one of R1 and R4 is a functional group for carrying a physiologically active substance,
$R2_{-1}$ and $R2_{-2}$ are independently a hydrogen atom, a methyl group, an ethyl group, or a propyl group,
R3 is a functional group derived from a hydrophilic compound,
R5 is a functional group imparting hydrophobicity, and
R6 is a halogen atom, or a functional group derived from the initiator in the synthesis of the emulsifier.

The main chain of the emulsifier, which can be used in the present invention, is composed of an alkyl chain.

The molecular weight (number average molecular weight) of the emulsifier, which can be used in the present invention, may be 1,000 to 1,000,000, preferably 1,500 to 500,000, more preferably 2,000 to 250,000, and most preferably 3,000 to 200,000.

With respect to the molecular weight distribution of the emulsifier, which can be used in the present invention, the polydispersity, Mw (weight average molecular weight)/Mn (number average molecular weight), may be 1 to 2, preferably 1.8 or less, and more preferably 1.5 or less. The emulsifier can be easily synthesized by a control/living radical polymerization or an ionic polymerization.

The hydrophilic segment of the emulsifier, which can be used in the present invention, is not particular limited, so long as it is hydrophilic as a whole. The length of the main chain and the graft chains (R3-R4) of the hydrophilic segment may be appropriately selected from conventional lengths, or arbitrarily synthesized.

The molecular weight of the hydrophilic segment may be 500 to 500,000, preferably 1,000 to 400,000, more preferably 2,000 to 300,000, and most preferably 3,000 to 250,000.

The integer m is 5 or more, preferably 5 to 500, and more preferably 10 to 300.

The graft chains of the hydrophilic segment contain a hydrophilic compound moiety, and has, as group R3, a functional group derived from the hydrophilic compound.

Examples of the hydrophilic compound, which can be used in the present invention, include oligoethylene glycol, polyethylene glycol, a 2-methacryloyloxyethyl phosphorylcholine (MPC) polymer, polyvinyl alcohol, polyvinyl pyrrolidone, polyamino acids, polypeptides, monosaccharides, polysaccharides, and the like. It can be appropriately selected from conventional hydrophilic compounds, so long as it is a synthesizable hydrophilic compound as the emulsifier, which can be used in the present invention.

The molecular weight of R3 is preferably 20 to 10,000, and more preferably 50 to 5,000.

The hydrophobic segment of the emulsifier, which can be used in the present invention, is not particular limited, so long as it is hydrophobic as a whole.

The molecular weight of the hydrophobic segment may be 500 to 500,000, preferably 1,000 to 400,000, more preferably 2,000 to 300,000, and most preferably 3,000 to 250,000.

The integer n is 5 or more, preferably 5 to 500, and more preferably 10 to 300.

The particle size of the polymer particles for carrying a physiologically active substance of the present invention can be controlled by selecting the molecular weight of the hydrophobic segment.

Group R1 or R4 in the general formula (1), i.e., the functional group for carrying a physiologically active substance, which can be used in the present invention, can be appropriately selected from known functional groups for carrying a physiologically active substance, and for example, a carboxyl group, a maleimide group, an amino group, a mercapto group, a hydroxyl group, an aldehyde group, an epoxy group, or the like, may be exemplified. According to the purpose, the type and the number can be appropriately selected. The amount of the functional group for carrying a physiologically active substance to be incorporated into a particle can be easily controlled.

When R1 or R4 is not the functional group for carrying a physiologically active substance, it can be appropriately selected from known atoms and functional groups, and for example, a hydrogen atom, a halogen atom, a methyl group, an ethyl group, a propyl group, or the like, may be exemplified.

Groups $R2_{-1}$ and $R2_{-2}$ are not particularly limited, so long as they do not inhibit the amphiphilic property of the emulsifier, or the function of the functional group for carrying a physiologically active substance, and for example, a hydrogen atom, a methyl group, an ethyl group, a propyl group, or the like, is preferable. $R2_{-1}$ and $R2_{-2}$ may be the same, or may be different from each other. It can be appropriately selected in accordance with each compound or a synthetic method.

Further, the graft chains of the hydrophobic segment has, as group R5, a functional group imparting hydrophobicity. Examples of the functional group imparting hydrophobicity include a hydrogen atom, a halogen atom, a methyl group, an ethyl group, a propyl group, a substituted or unsubstituted aromatic compound group, a carbonyl group, an amide group, an amino group, an aldehyde group, and a keto group; a functional group derived from each compound of amines, aldehydes, ketones, and ethers (for example, a group in which one or more atoms are removed from each of those compounds); and the like. Groups R5 may be the same groups, or may be different from each other.

The main chain and $R2_{-1}$ and R5 of the hydrophobic segment may be obtained, for example, by polymerizing monomers having one or more carbon double bonds. Examples of the monomer include ethylene, propylene, styrene sulfonic acid, styrene, methacrylate, acrylate, acrylamide, methacrylamide, and the like. These monomers may be used alone, or as a combination thereof.

The terminal group R6 of the hydrophobic segment of the emulsifier, which can be used in the present invention, may be appropriately selected from known ones in accordance with a polymerization method of an emulsifier. For example, a functional group derived from an initiating group used for the polymerization of an emulsifier, or a halogen atom may be exemplified. Alternatively, in accordance with a polymerization method used for the synthesis of the polymer particles, R6 may be appropriately selected from known ones. For example, in the case where it is covalently bonded to monomers in the synthesis of the polymer particles, one or more double bonds may be introduced.

The emulsifier, which can be used in the present invention, can be synthesized by a control/living radical polymerization or an ionic polymerization. Examples of the control/living radical polymerization include RAFT (Reversible Addition Fragmentation chain Transfer Polymerization), NMP (Nitroxide Mediated Polymerization), ATRP (Atom Transfer Radical Polymerization), and the like. By using an emulsifier synthesized by a control/living radical polymerization or an ionic polymerization polymer, the particles for carrying a physiologically active substance of the present invention having a narrow and uniform particle size distribution can be produced.

These synthetic methods can be appropriately selected in accordance with a functional group or the like for carrying a physiologically active substance, which is introduced into the hydrophilic segment.

Although the synthesis of the emulsifier, which can be used in the present invention, can be appropriately selected from known methods, there is a method in which the hydrophobic segment is initially synthesized, and then, the hydrophilic segment is synthesized; a method in which the hydrophilic segment is initially synthesized, and then, the hydrophobic segment is synthesized; and the like. A preferable method can be selected according to the purpose.

As the radical polymerization initiator, which can be used in the present invention, a radical polymerization initiator capable of being used in a common miniemulsion polymerization can be used, and examples thereof include a peroxide initiator, a persulfate initiator, an azo initiator, an azo low-temperature type initiator, and a redox initiator. In the present invention, since polymerization can be carried out at a temperature lower than a phase inversion emulsification temperature, a redox initiator or an azo low-temperature type initiator may be preferably used, but it is not particularly limited.

Examples of the peroxide initiator include benzoyl peroxide (BPO), di-t-butyl peroxide (DBPO), and ammonium peroxide. Examples of the persulfate initiator include potassium persulfate (KPS), ammonium persulfate (APS), and sodium persulfate (NPS).

Examples of the azo initiator include azobisisobutyronitrile (AIBN), dimethyl 2,2'-azobisisobutyrate (MAIB), 4,4'-azobis(4-cyanovaleric acid), and 2,2'-azobis(2,4-dimethylvaleronitrile). As the azo low-temperature type initiator, which can be used at a low temperature, among azo initiators, a water-soluble azo polymerization initiator VA-044 (Wako Pure Chemical Industries, Ltd.), an oil-soluble azo polymerization initiator V-70 (Wako Pure Chemical Industries, Ltd.), or the like may be exemplified.

Examples of the redox initiator include N,N,N',N'-tetramethylethylenediamine (TMEDA)/potassium persulfate (KPS), $FeSO_4$/KPS, $FeSO_4$/$H_2O_2$, ascorbic acid (vitamin C)/$H_2O_2$ or the like.

As the monomer, which can be used in the present invention, a monomer capable of being used in a common miniemulsion polymerization can be used. Examples thereof include styrene, styrene derivatives (for example, chloromethylstyrene and sodium styrene sulfonate), divinylbenzene, acrylic acid or methacrylic acid, itaconic acid, maleic anhydride, maleic acid, phthalic acid, acrylic acid esters or methacrylic acid esters [for example, methyl (meth)acrylate, ethyl (meth)acrylate, butyl (meth)acrylate, and hexadecyl (meth)acrylate], and vinyl acetate. These monomers can be used as a combination of two or more.

The method of preparing polymer particles for carrying a physiologically active substance of the present invention is not particularly limited, so long as the polymer particles for carrying a physiologically active substance of the present invention can be prepared, and it can be carried out in a similar fashion to that of a conventional miniemulsion polymerization (for example, M. Antonietti, K. Landfester, Prog. Polym. Sci., 2002, 27, 689-757; or J. M. Asua, Prog. Polym. Sci., 2002, 27, 1283-1346), except that the emulsifier capable of being used in the present invention is used in the polymerization reaction. Since microparticles can be prepared by a low energy process, in which a high shear force using a powerful emulsifying device is not required, a phase inversion emulsification method or a phase inversion temperature emulsification method, in particular, a phase inversion temperature emulsification method (for example, L. Spernath, S. Magdassi, Polym. Adv. Technol., 2007, 18, 705-711) is preferably used.

The common miniemulsion polymerization is by no means limited to the following, but can comprise, for example, the steps of: mixing a monomer, a radical polymerization initiator, and an emulsifier; shearing the mixture; and heating the mixture to the polymerization initiation temperature to polymerize the mixture. In the miniemulsion polymerization, after the mixing of the monomer for polymerization with the emulsifier, for example, a shearing step by ultrasonic irradiation is carried out, and as a result, the monomer is torn off by the shearing force, and monomer micro oil droplets covered with the emulsifier are formed. Next, the monomer micro oil droplets can be polymerized by heating the mixture to the polymerization initiation temperature of the radical polymerization initiator, to obtain the polymer particles.

In the phase inversion temperature emulsification method, for example, by utilizing a change in curvature of a surfactant caused by external environments (the composition of water/oil, temperature, pressure, electrolyte concentration, and chemical reactions), the continuous phase is changed from an oil phase to a water phase to form an O/W type emulsion, and polymerization is carried out by adding the initiator to obtain the polymer particles.

The reaction conditions in the polymerization of the polymer particles, for example, a solvent, a mixing ratio, temperature, a reaction time, and the like, may be appropriately determined, according to the monomer to be used, as well as the kind of the functional group for carrying a physiologically active substance, the initiator, the emulsifier, the average particle size of the polymer particles to be synthesized, the amount of the physiologically active substance to be carried on the surface of the particles, and the like, by carrying out, for example, a pilot test.

An analytical reagent can be prepared according to a known method, except that the polymer particles for carrying a physiologically active substance of the present invention are used.

The analytical reagent as used herein means a reagent for analyzing a substance to be analyzed contained in a biological sample, wherein a physiologically active substance capable of reacting with the substance to be analyzed is carried on the polymer particles for carrying a physiologically active substance.

The combination of the physiologically active substance and the substance to be analyzed, as well as the reaction of the physiologically active substance with the functional group for carrying a physiologically active substance, can be appropriately selected from known methods.

As the physiologically active substance, which can be used in embodiments of the present invention, a substance capable of reacting with the substance to be analyzed contained in a biological sample, for example, an antigen, an antibody, an enzyme, a receptor, DNA, RNA, a sugar chain, or the like, can be exemplified.

Examples of the substance to be analyzed contained in a biological sample, which can be used in embodiments of the present invention, include IgG, C reactive protein (CRP), ferritin, β-2 microglobulin, α-fetoprotein (AFP), IgE, hepatitis B virus (HBS antibody or HBc antibody), D dimer, fibrin/fibrinogen degradation products (FDP), soluble fibrin (SF), plasmin/α2-plasmin inhibitor complex (PPI), prostate specific antigen (PSA), elastase 1, elastase XDP, thrombomodulin, albumin (preferably serum albumin), and the like.

For example, in the case where an antibody is used as the physiologically active substance, a monoclonal antibody or a polyclonal antibody may be used. As the type of the antibody, an Immunoglobulin molecule per se, as well as its antibody fragments, such as Fab, Fab', F(ab')2, Fv, or the like, may be used. For example, in the case where DNA is used as the physiologically active substance, a DNA probe consisting of about 5 to 100 bases and complementary to the physiologically active substance, may be used.

The sample to be analyzed, which can be used and analyzed in embodiments of the present invention, is not particularly limited, so long as it is a sample suspected of containing the substance to be analyzed. In particular, a biological sample, for example, blood, serum, plasma, urine, spinal fluid, lysate of cells or a tissue, or the like, may be exemplified.

The analytic reagent, which can be used in embodiments of the present invention, may be used in a known latex method (for example, a latex agglutination method, or a B/F separation using latex).

In the latex agglutination method, the amount of the substance to be analyzed contained in a sample to be analyzed can be analyzed (in particular, measured) by optically analyzing (in particular, measured) the degree of agglutination caused when the analytical reagent is brought into contact with the sample to be analyzed in liquid. As a concrete method of optically detecting the degree of agglutination of latex particles, it can be measured using an optical device for measuring, for example, scattered light intensity, absorbance, or transmitted light intensity. The preferred measuring wavelength is 300 to 800 nm. In the measurement, according to a conventional method, the measurement can be carried out by setting the particle size (average particle size) or the concentration of the latex particles, or a reaction time, and measuring an increase or decrease in scattered light intensity, absorbance, or transmitted light intensity. Further, these methods may be combined.

In the B/F separation using latex, the amount of the substance to be analyzed contained in a sample to be analyzed can be analyzed (in particular, measured) by bringing the analytical reagent into contact with the sample to be analyzed in liquid, separating the latex particles from the liquid by B/F separation, and analyzing (in particular, measuring) the substance to be analyzed that is bonded to the latex particles, or the substance to be analyzed that remains in the liquid.

EXAMPLES

The present invention now will be further illustrated by, but is by no means limited to, the following Examples.

Example 1

Synthesis of Emulsifier (Amphiphilic Block Polymer)

In this Example, after an emulsifier (amphiphilic block polymer: $PSt_{21}$-b-$POEGMA_{41}$-Cl) was synthesized, a w-terminal aminated amphiphilic block polymer $PSt_{21}$-b-$POEGMA_{41}$-$NH_2$ was synthesized by a Gabriel synthesis, in accordance with the following reaction scheme.

[Chem. 4]

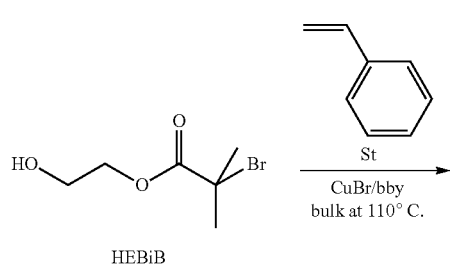

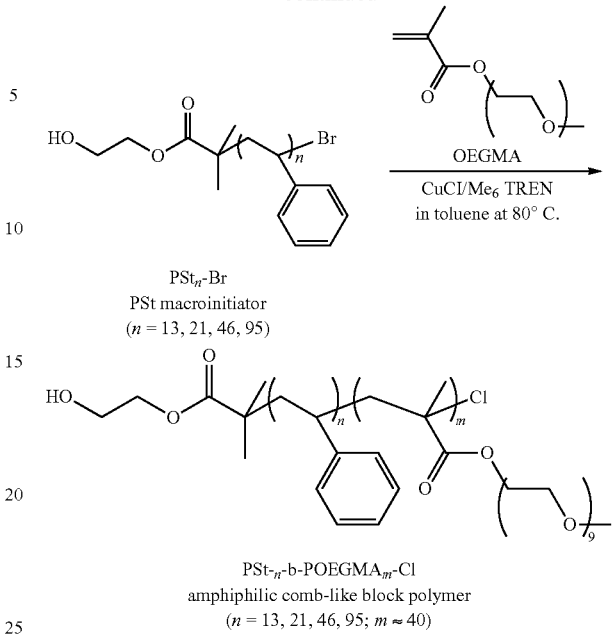

Under a nitrogen atmosphere, 2 g of 2,2'-bipyridine (bpy) and 0.6 g of CuBr were added to 10 g of styrene (KANTO CHEMICAL CO., INC.) and 1 g of HEBiB (2-hydroxyethyl-2-bromoisobutyrate), as an initiator, to carry out polymerization at 110° C. In connection with this, HEBiB synthesized from BiB (2-bromoisobutyryl bromide) and ethylene glycol was used. After the completion of the polymerization, the reaction mixture was diluted with tetrahydrofuran (THF), and re-precipitated in methanol to obtain $PSt_{21}$-Br.

Next, 0.66 g of $PSt_{21}$-Br, 7.0 g of OEGMA (oligo(ethylene glycol) methyl ether methacrylate (degree of polymerization: 9): Shin-Nakamura Chemical Co., Ltd.), 0.14 g of $Me_6TREN$ (tris(2-N,N-dimethylamino)ethyl)amine: Chiba University), and 0.03 g of CuCl were mixed in 12 mL of toluene (KANTO CHEMICAL CO., INC.) to carry out polymerization at 80° C. for 24 hours.

After the completion of the polymerization, the reaction mixture was dissolved in THF, and passed through an alumina column to remove a cupper complex. The eluate was re-precipitated in hexane, dissolved in toluene, and dialyzed in a 1:1 solvent of toluene/methanol, and the obtained solution was concentrated using an evaporator to obtain an amphiphilic block polymer $PSt_{21}$-b-$POEGMA_{41}$-Cl.

Next, 0.07 g of KPHI (potassium phthalimide) and 5 mL of N,N-dimethylformamide (DMF) were added to 0.80 g of $PSt_{21}$-b-$POEGMA_{41}$-Cl, and the mixture was stirred at 50° C. for 16 hours. Unreacted KPHI was removed by adding 15 mL of toluene. Further, dialysis was carried out in a 1:1 solvent of toluene/methanol. The obtained solution was concentrated using an evaporator.

To the concentrate, 0.02 g of $H_2N$—$NH_2.H_2O$ and 6 mL of DMF were added, and the mixture was stirred at 50° C. for 16 hours. Toluene was added to the reaction mixture, and dialysis was carried out in a 1:1 solvent of toluene/methanol. The obtained solution was concentrated using an evaporator to obtain an amphiphilic block polymer $PSt_{21}$-b-$POEGMA_{41}$-$NH_2$ having an amino group at the w-terminus.

Example 2

Synthesis of Latex Particles Using Emulsifier

After 0.05 g of $PSt_{21}$-b-$POEGMA_{41}$-$NH_2$ prepared in Example 1 was dissolved in 0.1 g of styrene, 1.2 g of ultrapure water was further added. The mixture was heated to 90° C., and stirred for 10 minutes to obtain a W/O type emulsion.

Next, phase inversion emulsification was carried out by stirring in an ice bath to obtain an O/W type emulsion. To the emulsion, 0.03 g of a water-soluble initiator (VA-044: Wako Pure Chemical Industries, Ltd.) was added to carry out polymerization at 40° C. for 6 hours.

The particle size of the obtained latex particles was measured using a dynamic light scattering device (DLS: ELSZ-1000ZSCK light scattering apparatus Otsuka), and was 52±20 nm.

Example 3

Effect of Chain Length of Hydrophobic Segment of Emulsifier on Particle Size Amphiphilic block polymers as shown in Table 1, said polymers having 13, 21, 46, or 95 repeating units (corresponding to n in the general formula (1)) of polystyrene in the hydrophobic segment and 42, 41, 45, or 36 repeating units (corresponding to m in the general formula (1)) of polystyrene in the hydrophilic segment, were synthesized in accordance with Example 1. In connection with this, OEGMA (degree of polymerization: 9) was used as the graft moiety. The repeating units of the hydrophobic segment were controlled by setting the molar ratio (M/I ratio) of a monomer (styrene)/initiator (HEBiB) to the values as shown in Table 1. The repeating units of the hydrophilic segment were controlled by unifying the molar ratio of a monomer (OEGMA)/initiator (PSt-Br) to 50.

Next, latex particles of the combinations as shown in Table 1, i.e., the combination of PSt13 and OEGMA42, the combination of PSt21 and OEGMA41, the combination of PSt46 and OEGMA45, and the combination of PSt95 and OEGMA36, were synthesized in accordance with Example 2.

The particle size was measured using a dynamic light scattering device (DLS). The particle size distributions of the latex particles were shown in the FIGURE, and the particle sizes were shown in Table 1. Four peaks shown in the FIGURE were the results of $PSt_{13}$-b-$POEGMA_{42}$-Cl, $PSt_{21}$-b-$POEGMA_{41}$-Cl, $PSt_{46}$-b-$POEGMA_{45}$-Cl, and $PSt_{95}$-b-$POEGMA_{36}$-Cl from the left. It was found that latex particles having an average particle size of 32 nm to 120 nm could be synthesized. Further, Mw/Mn was about 1.4, and it was found that latex particles having a narrow particle size distribution could be synthesized. Furthermore, it was found that the particle size of latex particles increased according to the chain length of the hydrophobic segment. Mn represents a number average molecular weight, Mw represents a weight average molecular weight, and Mw/Mn represents polydispersity.

TABLE 1

| Sample | M/I ratio | Mw/Mn | Particle size (nm) |
|---|---|---|---|
| $PSt_{13}$-b-$POEGMA_{42}$-Cl | 10 | 1.48 | 32 ± 11 |
| $PSt_{21}$-b-$POEGMA_{41}$-Cl | 20 | 1.45 | 52 ± 19 |
| $PSt_{46}$-b-$POEGMA_{45}$-Cl | 50 | 1.37 | 83 ± 36 |
| $PSt_{95}$-b-$POEGMA_{36}$-Cl | 100 | 1.43 | 120 ± 54 |

Example 4

Introduction of HRP into Latex Particles

In accordance with Example 1, 24 equivalents of a monomer (OEGMA) to an initiator ($PSt_{20}$-Br) was added to prepare $PSt_{20}$-b-$POEGMA_{24}$-$NH_2$. Next, latex particles (particle size=22±6 nm) were synthesized in a similar fashion to that of Example 2. Dispersed was 0.5 mg of the latex particles to a sodium phosphate buffer (pH=7.00).

Next, activated horseradish peroxidase (HRP: EZ-Link Plus Activated Peroxidase (manufactured by Thermo scientific)) having an aldehyde group was added to the latex particles at 10-fold of the particle number. After the mixture was allowed to stand at room temperature for 1 hour, an excess amount of a sodium borohydride aqueous solution was added. The mixture was allowed to stand at 5° C. for 1 hour, and was subjected to purification using a hollow fiber filter (20 mmol/L sodium phosphate buffer, 0.1% Tween20) to obtain HRP-immobilized polymer particles.

To 100 µL of the obtained polymer particles dispersion ($8\times10^8$ particles/mL), 200 µL of tetramethylbenzidine (TMB) was added. After 30 minutes, the reaction was stopped by adding 200 µL of a 200 mmol/L sulfuric acid aqueous solution. An absorbance of the solution at 450 nm increased (OD=0.8). It was confirmed from this that HRP was chemically introduced onto the surface of the latex particles.

Although the present invention has been described with reference to specific embodiments, various changes and modifications obvious to those skilled in the art are possible without departing from the scope of the appended claims.

The invention claimed is:

1. Polymer particles for covalently bonding a physiologically active substance, said polymer particles being obtained by polymerizing a monomer, a radical polymerization initiator, and an emulsifier, wherein the emulsifier is an amphiphilic block polymer of the general formula (1):

[Chem. 1]

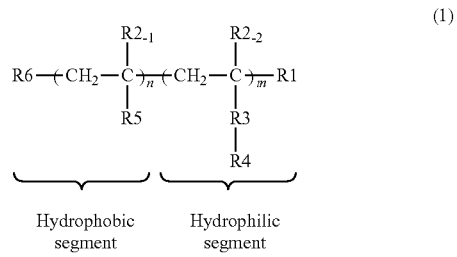

(1)

Hydrophobic segment    Hydrophilic segment wherein n is an integer of 5 or more,
m is an integer of 5 or more,
R1 and R4 are independent, and at least one of R1 and R4 is a functional group for covalently bonding a physiologically active substance, wherein the functional group for covalently bonding a physiologically active substance is selected from the group consisting of a carboxyl group, a maleimide group, an amino group, a mercapto group, a hydroxyl group, an aldehyde group, and an epoxy group, $R2_{-1}$ and $R2_{-2}$ are independently a hydrogen atom, a methyl group, an ethyl group, or a propyl group, when R1 is not the functional group for covalently bonding a physiologically active substance, R1 is selected from the group consisting of a hydrogen atom, a methyl group, an ethyl group, and a propyl group, when R4 is not the functional group for covalently bonding a physiologically active substance, R4 is selected from the group consisting of a hydrogen atom, a halogen atom, a methyl group, an ethyl group, and a propyl group, R3 is a functional group derived from a hydrophilic compound, R5 is a functional group imparting hydrophobicity, and R6 is a halogen atom, or a functional group derived from the initiator in the synthesis of the emulsifier.

2. The polymer particles for covalently bonding a physiologically active substance according to claim 1, wherein the hydrophilic compound in R3 is a compound selected from the group consisting of oligoethylene glycol, polyethylene glycol, a 2-methacryloyloxyethyl phosphorylcholine polymer, polyvinyl alcohol, polyvinyl pyrrolidone, polyamino acids, polypeptides, monosaccharides, and polysaccharides.

3. The polymer particles for covalently bonding a physiologically active substance according to claim 1, wherein R5 is one or more functional groups selected from the group consisting of a hydrogen atom, a halogen atom, a methyl group, an ethyl group, a propyl group, a substituted or unsubstituted aromatic compound group, a carbonyl group, an amide group, an amino group, an aldehyde group, and a keto group, and a functional group derived from each compound of amines, aldehydes, ketones, and ethers.

4. The polymer particles for covalently bonding a physiologically active substance according to claim 1, the number average molecular weight of the emulsifier is 1,000 to 1,000,000.

5. The polymer particles for covalently bonding a physiologically active substance according to claim 1, the number average molecular weight of the hydrophilic segment is 500 to 500,000.

6. The polymer particles for covalently bonding a physiologically active substance according to claim 1, the number average molecular weight of the hydrophobic segment is 500 to 500,000.

7. A method of preparing polymer particles for covalently bonding a physiologically active substance, said method comprising:

mixing a monomer, a radical polymerization initiator, and an emulsifier;

shearing the mixture; and heating the mixture to the polymerization initiation temperature to polymerize the mixture, to obtain the polymer particles for covalently bonding a physiologically active substance, wherein the emulsifier is a compound of the general formula (1):

[Chem. 1]

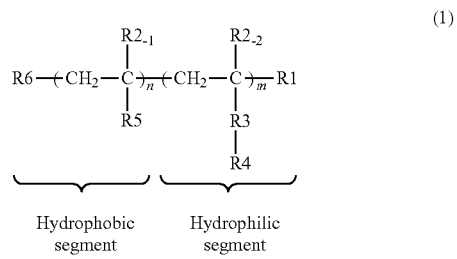

wherein n is an integer of 5 or more, m is an integer of 5 or more,

R1 and R4 are independent, and at least one of R1 and R4 is a functional group for covalently bonding a physiologically active substance, wherein the functional group for covalently bonding a physiologically active substance is selected from the group consisting of a carboxyl group, a maleimide group, an amino group, a mercapto group, a hydroxyl group, an aldehyde group, and an epoxy group, $R2_{-1}$ and $R2_{-2}$ are independently a hydrogen atom, a methyl group, an ethyl group, or a propyl group, when R1 is not the functional group for covalently bonding a physiologically active substance, R1 is selected from the group consisting of hydrogen atom, a methyl group, an ethyl group, and a propyl group, when R4 is not the functional group for covalently bonding a physiologically active substance, R4 is selected from the group consisting of a hydrogen atom, a halogen atom, a methyl group, an ethyl group, and a propyl group, R3 is a functional group derived from a hydrophilic compound, R5 is a functional group imparting hydrophobicity, and R6 is a halogen atom, or a functional group derived from the initiator in the synthesis of the emulsifier.

8. The method according to claim 7, wherein the synthesis of the emulsifier is a control/living radical polymerization or an ionic polymerization.

9. The method according to claim 7, wherein the miniemulsion polymerization is a phase inversion emulsification method.

* * * * *